US009810644B2

(12) United States Patent
Mohamed Salleh et al.

(10) Patent No.: US 9,810,644 B2
(45) Date of Patent: Nov. 7, 2017

(54) METHOD AND APPARATUS FOR INSPECTING A COMPONENT HAVING A CELLULAR STRUCTURE

(71) Applicant: ROLLS-ROYCE plc, London (GB)

(72) Inventors: Najib Bin Mohamed Salleh, Derby (GB); João Paulo Siqueira Cezario, Derby (GB)

(73) Assignee: ROLLS-ROYCE plc, London (GB)

( * ) Notice: Subject to any disclaimer, the term of this patent is extended or adjusted under 35 U.S.C. 154(b) by 0 days.

(21) Appl. No.: 15/255,808

(22) Filed: Sep. 2, 2016

(65) Prior Publication Data
US 2017/0089844 A1    Mar. 30, 2017

(30) Foreign Application Priority Data

Sep. 29, 2015 (GB) .................................. 1517159.8

(51) Int. Cl.
| *G01N 21/00* | (2006.01) |
| *G01N 21/956* | (2006.01) |
| *F01D 11/12* | (2006.01) |
| *G01N 1/28* | (2006.01) |
| *G01N 21/88* | (2006.01) |
| *G01M 13/00* | (2006.01) |

(52) U.S. Cl.
CPC ..... *G01N 21/95692* (2013.01); *F01D 11/127* (2013.01); *G01M 13/005* (2013.01); *G01N 1/28* (2013.01); *G01N 21/8806* (2013.01); *F05D 2220/32* (2013.01); *F05D 2260/83* (2013.01)

(58) Field of Classification Search
CPC . G01M 3/04; G01N 21/8806; G01N 21/8803; G01N 21/95692; G01N 21/954; G01N 1/28; B01D 46/2418; F01D 11/127

USPC .............. 356/237.1–237.6, 241.1; 73/37, 40
See application file for complete search history.

(56) References Cited

U.S. PATENT DOCUMENTS

| 5,078,005 A | 1/1992 | Krempel et al. |
| 5,275,489 A | 1/1994 | Borneman et al. |
| 5,315,861 A | 5/1994 | Egan et al. |
| 5,398,541 A * | 3/1995 | Hijikata ............. B01D 46/0063 73/38 |
| 5,419,181 A * | 5/1995 | Egan ...................... G01M 3/04 73/37 |
| 6,452,670 B1 * | 9/2002 | Bour ...................... G01M 3/38 356/237.1 |

(Continued)

FOREIGN PATENT DOCUMENTS

CN    103837549 A    6/2014

OTHER PUBLICATIONS

Feb. 11, 2016 Search Report issued in British Patent Application No. 1517159.8.

*Primary Examiner* — Hoa Pham
(74) *Attorney, Agent, or Firm* — Oliff PLC (57) ABSTRACT

A method of inspecting a component comprising a cellular structure bonded to a carrier substrate to form a matrix of open-ended cells is described. The method comprises: submerging the component in an inspection liquid disposed within a pressure vessel; changing the pressure within the pressure vessel; withdrawing the component from the inspection liquid; and determining whether the cells of the component are filled with the inspection liquid. A corresponding inspection apparatus is also described.

20 Claims, 9 Drawing Sheets

(56) References Cited

U.S. PATENT DOCUMENTS

| | | | | |
|---|---|---|---|---|
| 7,596,274 B2* | 9/2009 | Kondo | ............ | G01N 21/95692 296/39.1 |
| 8,049,878 B2* | 11/2011 | Zoeller, III | ...... | G01N 21/95692 356/237.1 |
| 8,561,456 B2* | 10/2013 | Meredith | .............. | G01M 3/047 356/328 |
| 2007/0022724 A1* | 2/2007 | Gargano | ............ | B01D 46/0086 55/523 |
| 2015/0013435 A1* | 1/2015 | Sugiyama | .......... | B01D 46/2418 73/40 |

* cited by examiner

METHOD AND APPARATUS FOR INSPECTING A COMPONENT HAVING A CELLULAR STRUCTURE

The disclosure relates a method and apparatus for inspecting a component having a cellular structure and particularly, but not exclusively, for inspecting a metallic honeycomb seal for use in a gas turbine engine.

It is desirable in gas turbine engines to minimise the clearance between rotating and static components in order to improve efficiency. However, the reduction of clearances between the rotating and static components increases the risk of contact between the components. To overcome this issue, it is common for the static component, such as the casing of the turbine, to be provided with an abradable structure, such as a metallic honeycomb seal, in order to reduce damage to the rotating components, i.e. rotor blades.

Metallic honeycomb seals are typically formed by brazing a honeycomb foil structure, having a matrix of hexagonal cells, to a carrier substrate, such as a ring (seal rings) or sheet (seal segments). It is important that the honeycomb foil structure is properly sealed to the carrier substrate during the brazing process in order for the seal to perform its function. Therefore, the honeycomb seals are inspected after the brazing process to ensure that no leaks are present between adjacent cells. As the honeycomb foil structure is abraded during use, it is common to replace the honeycomb foil structure periodically, while utilising the existing carrier substrate. The inspection process must therefore be repeated after such maintenance actions.

In a conventional method of inspection, the honeycomb seal is submerged in an inspection liquid such that the cells of the honeycomb seal are filled with the inspection liquid. The seal is then removed from the liquid and left to stand at 45 degrees for a minimum of 5 minutes. The seal is then examined by shining a light (having an intensity of 500 lux) at the cells. Those cells which are properly brazed retain the inspection liquid, whereas those cells which are not properly brazed are empty. Consequently, the full, properly brazed cells reflect the light and thus appear bright. In contrast, the empty, improperly brazed cells do not reflect the light and so appear dark.

The cells can therefore be inspected and a determination made as to whether the braze has been properly formed.

Trapped air bubbles at the base of the honeycomb cells introduce a false reading as the cells appear empty, when they are in fact properly brazed. In order to remove trapped air bubbles from the honeycomb cells, the inspection liquid may be agitated or a liquid jet directed at the cells. However, air bubbles may still be in the honeycomb cell even under agitation and pressure spray.

Further, the existing method requires a technician to ensure that every honeycomb cell is fully filled with the inspection liquid. Owing to the large number of honeycomb cells, the probability of making an error is high.

Moreover, the existing method has difficulty in removing all of the trapped air bubbles from seals having a relatively tall honeycomb cell (typically 0.032"). As a result, additional time is required to ensure the pressure spray gets all of the bubbles out of the honeycomb cells.

It is therefore desired to provide a method of inspection and apparatus which overcomes some or all of the problems associated with the prior art methods.

Therefore, in accordance with an aspect of the disclosure, there is provided a method of inspecting a component comprising a cellular structure bonded to a carrier substrate to form a matrix of open-ended cells, the method comprising: submerging the component in an inspection liquid disposed within a pressure vessel; changing the pressure within the pressure vessel; withdrawing the component from the inspection liquid; and determining whether the cells of the component are filled with the inspection liquid.

The cells of the component may be filled with inspection liquid when the component is submerged and the pressure in the pressure vessel may be decreased so as to release trapped air from within the cells.

A first stream of gas may be directed at the cells such that the inspection liquid is displaced by the air from any cells which are not properly bonded to the carrier substrate.

Cells which are filled with the inspection liquid may be properly bonded to the carrier substrate and cells which are not filled with the inspection liquid may not be properly bonded to the carrier substrate.

A second stream of gas may be directed at the cells, the second stream of gas having a higher pressure than the first stream of gas such that the inspection liquid is displaced also from cells which are properly bonded to the carrier substrate.

The component may be submerged in the inspection liquid such that at least some of the cells of the component are filled with air and thus prevent the inspection liquid from entering the cells, and the pressure in the pressure vessel may be increased such that the trapped air is compressed and, for cells which are not properly bonded to the carrier substrate, forced into adjacent cells and replaced by inspection liquid.

Cells which are filled with the inspection liquid may not be properly bonded to the carrier substrate and cells which are not filled with the inspection liquid may be properly bonded to the carrier substrate. The properly bonded cells will thus remain dry and therefore reduce the quantity of liquid which must be removed from the cells.

A stream of gas may be directed at the cells such that the inspection liquid is displaced from cells which are not properly bonded to the carrier substrate.

Determining whether the cells of the component are filled with the inspection liquid may be performed using a probe comprising a camera which is used to detect whether the cells are filled with the inspection liquid.

The probe may comprise a light source which is used to illuminate the cells being viewed by the camera.

The probe may be movable (e.g. rotatable and/or translatable) so as to direct the camera towards each of the cells of the component.

The camera of the probe may be used to detect that all of the cells are empty following inspection of the component.

In accordance with another aspect of the disclosure, there is also provided an inspection apparatus for inspecting a component comprising a cellular structure bonded to a carrier substrate to form a matrix of open-ended cells, the apparatus comprising: a pressure vessel configured to contain an inspection liquid into which the component is submerged; a pump connected to the pressure vessel and configured to change the pressure within the vessel; and a probe comprising a camera for determining whether the cells of the component are filled with the inspection liquid.

The pump may be configured to decrease the pressure in the pressure vessel so as to release trapped air from within the cells of the component which are filled with inspection liquid when the component is submerged.

The cells which are filled with the inspection liquid may be determined as being properly bonded to the carrier substrate and cells which are not filled with the inspection liquid may be determined as being not properly bonded to the carrier substrate.

The probe may further comprise a gas ejector configured to direct a first stream of gas at the cells such that the inspection liquid is displaced by the air from any cells which are not properly bonded to the carrier substrate.

The gas ejector may be further configured to direct a second stream of gas at the cells, the second stream of gas having a higher pressure than the first stream of gas such that the inspection liquid is displaced also from cells which are properly bonded to the carrier substrate.

The pump may be configured to increase the pressure within the pressure vessel so as to compress air trapped in the cells as the component is submerged in the inspection liquid such that the trapped air is compressed and, for cells which are not properly bonded to the carrier substrate, forced into adjacent cells and replaced by inspection liquid.

The cells which are filled with the inspection liquid may be determined as being not properly bonded to the carrier substrate and cells which are not filled with the inspection liquid may be determined as being properly bonded to the carrier substrate. The properly bonded cells will thus remain dry and therefore reduce the quantity of liquid which must be removed from the cells.

The probe may further comprise a gas ejector configured to direct a stream of gas at the cells such that the inspection liquid is displaced from cells which are not properly bonded to the carrier substrate.

The probe may further comprise a light source which is used to illuminate the cells being viewed by the camera.

The probe may be movable (e.g. rotatable and/or translatable) so as to direct the camera towards each of the cells of the component.

The camera may be further configured to detect whether all of the cells are empty following inspection of the component.

For a better understanding of the invention, and to show more clearly how it may be carried into effect, reference will now be made, by way of example, to the accompanying drawings, in which.

Figure 1:
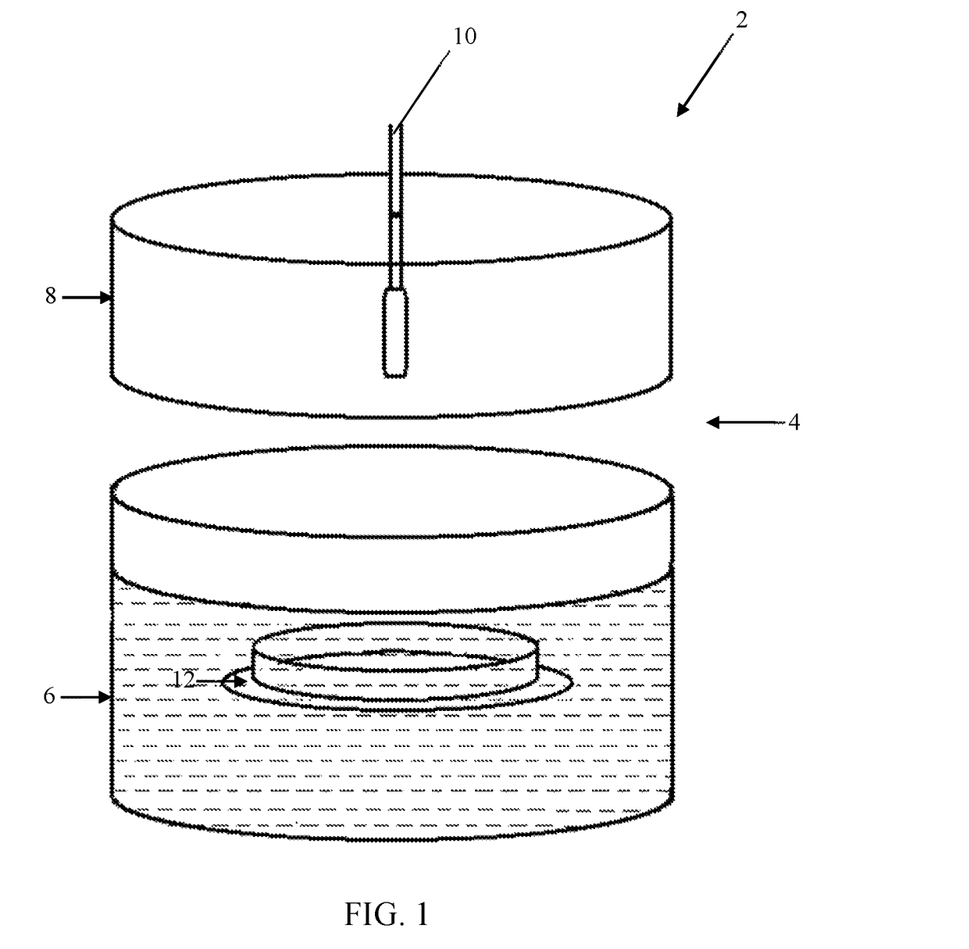
FIG. 1 is a perspective view of an inspection apparatus during a first stage of inspecting a seal.

FIG. 1 shows an inspection apparatus 2. The inspection apparatus 2 comprises a pressure vessel 4 having a lower tank section 6 and an upper lid section 8. The lower tank section 6 is filled with an inspection liquid. The inspection apparatus 2 further comprises an inspection probe 10 which extends into the interior of the pressure vessel 4 through the upper lid section 8.

A honeycomb seal in the form of a ring 12 is placed in the lower tank section 6 and submerged in the inspection liquid. The seal ring 12 is arranged such that the honeycomb cells extend radially inwards towards the centre of the lower tank section 6. The lower tank section 6 and the upper lid section 8 are then sealed to one another and the pressure reduced from atmospheric pressure (~1 bar) using a pump (not shown). The pressure within the pressure vessel 4 is reduced in steps and allowed to settle for approximately 3 to 5 minutes following each reduction in pressure. The negative pressure within the pressure vessel 4 causes any air trapped within the honeycomb cells to be released.

Figure 2:
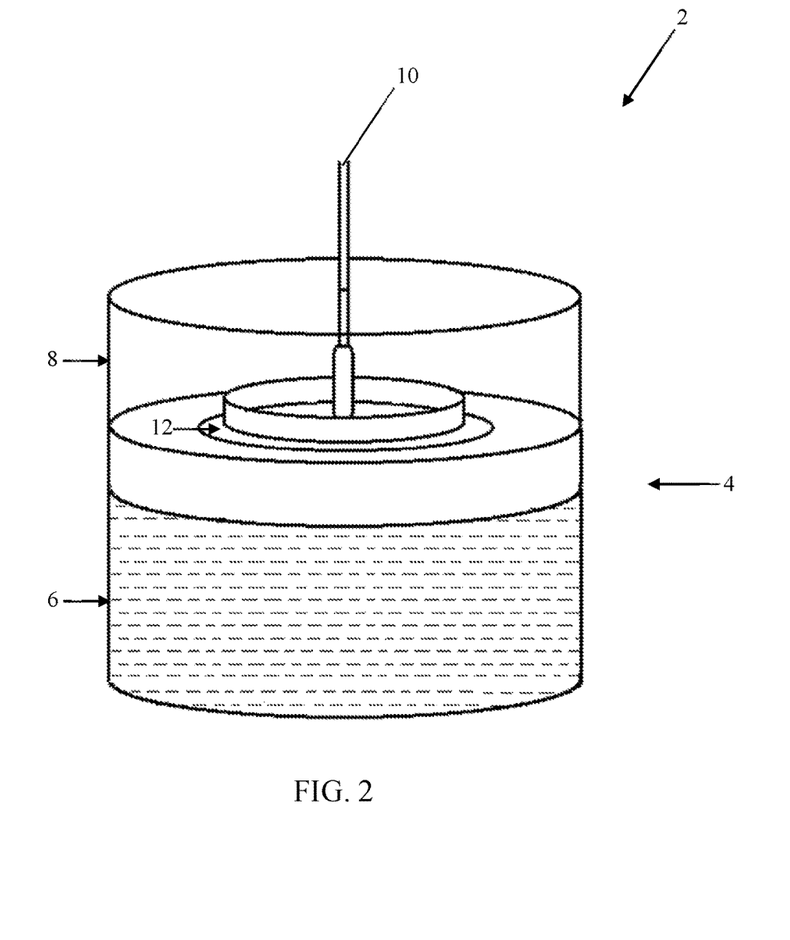
FIG. 2 is a perspective view of the inspection apparatus during a second stage of inspecting the seal.
Figure 3:
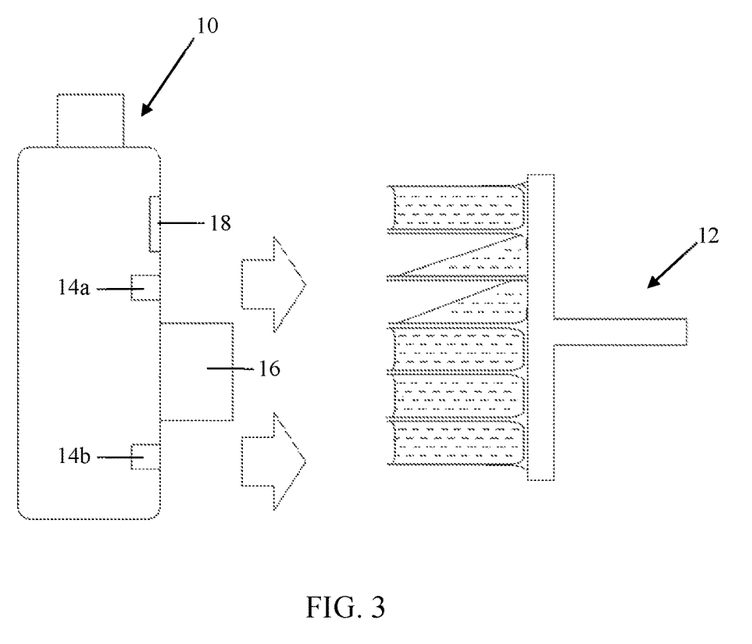
FIG. 3 is a side view of a probe of the apparatus during a third stage of inspecting the seal.

As shown in FIG. 2, the seal ring 12 is then lifted out of the inspection liquid and the pressure vessel 4 decompressed to atmospheric pressure. The probe 10 is provided with upper and lower ejectors 14a, 14b which direct air radially outwards towards the honeycomb cells of the seal ring 12. As shown in FIG. 3, the ejectors 14a, 14b direct a low pressure airstream over the honeycomb cells. This causes any improperly brazed cells to leak, whereas surface tension is sufficient in properly brazed cells to retain the inspection liquid. In FIG. 3, the second and third cells (from the top) are poorly brazed and so allow the inspection liquid to leak between the cells. As a result, the airstream from the ejectors 14a, 14b forces the inspection liquid to flow between the cells, thus causing the inspection liquid to leak from the cells. In contrast, the remaining (first, fourth, fifth and sixth) cells are properly brazed and so the airstream does not cause any of the inspection liquid to be released from the cells.

Figure 4:
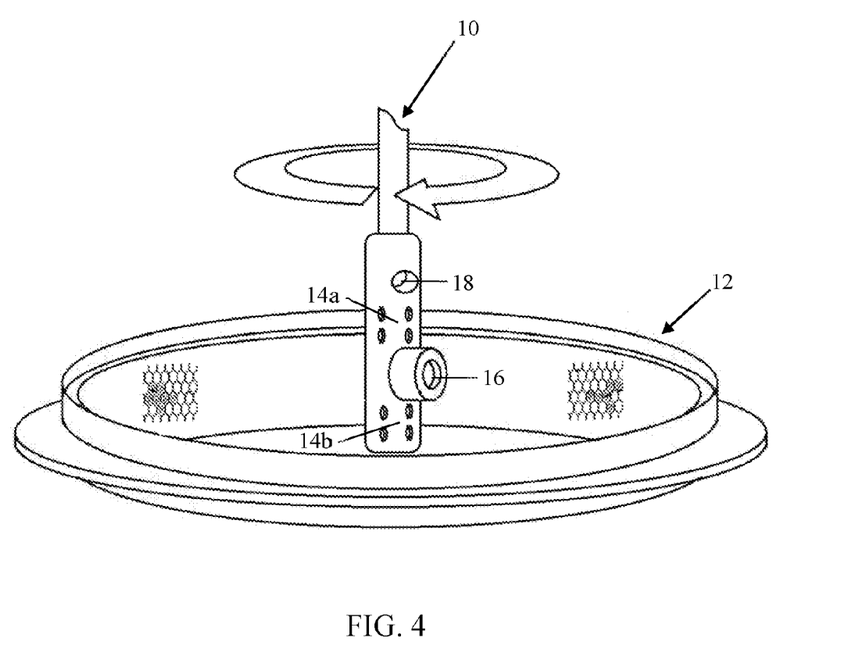
FIG. 4 is a perspective view of the probe of the apparatus during a fourth stage of inspecting the seal.
Figure 5:
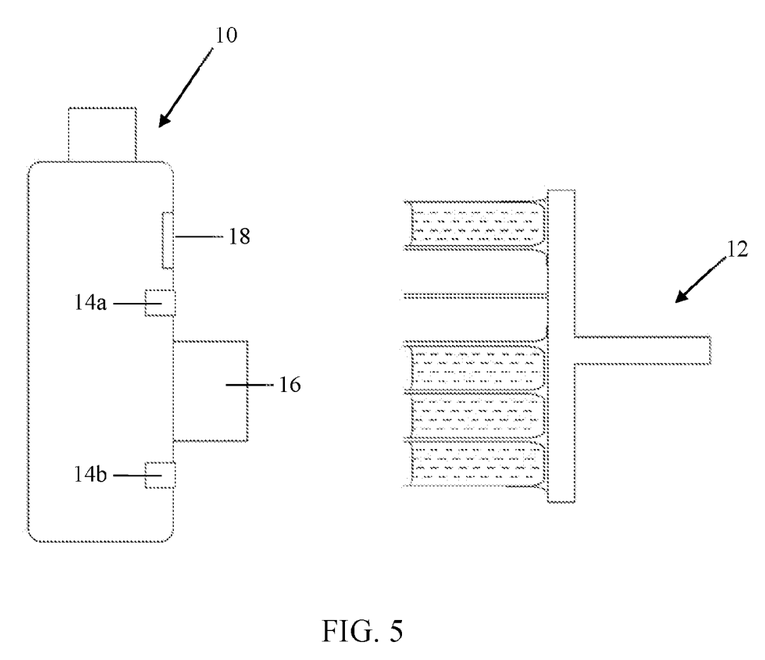
FIG. 5 is a side view of the probe during the fourth stage of inspecting the seal.

As shown in FIGS. 4 and 5, the probe 10 further comprises a camera 16 and a light source 18. The light source 18 projects light over the cells of the seal ring 12. Cells containing the inspection liquid reflect the light back towards the probe 10 and thus appear bright to the camera 16. In contrast, any cells which have leaked and are therefore empty do not reflect as much light back towards the probe 10 and thus appear dark to the camera 16.

As shown in FIG. 4, the probe 10 is fully rotatable (360°) about its axis. The probe 10 is therefore rotated so that each and every cell is exposed to the light source 18 and visible to the camera 16. The output of the camera 16 thus allows a determination to be made as to whether each cell of the seal ring 12 is properly brazed. The angular position of the camera 16 allows the exact location of any defective cells to be easily identified. The camera 16 may be connected to a processor which automatically analyses the output of the camera 16 and determines whether there are any failed brazes and their location. The low light conditions within the pressure vessel 4 aid the inspection process.

Figure 6:
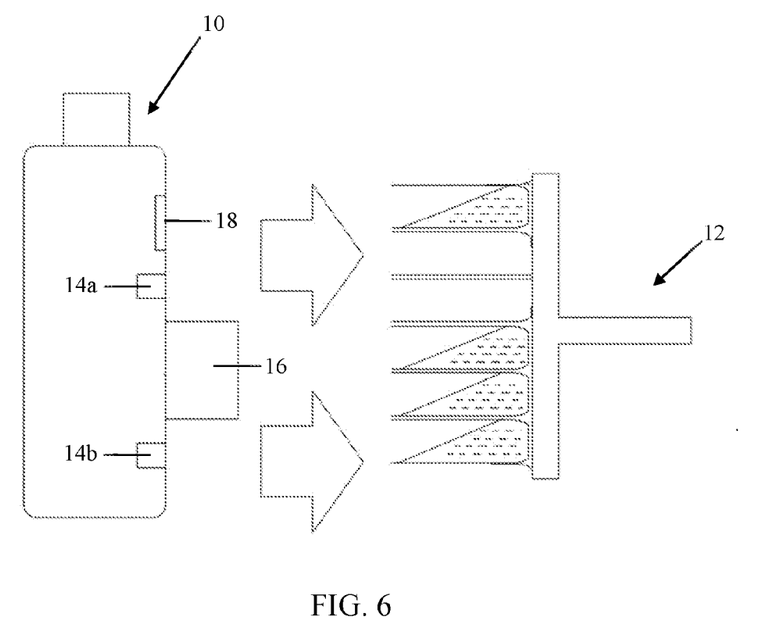
FIG. 6 is a side view of the probe during a fifth stage of inspecting the seal.

Once the inspection of the seal ring 12 is complete, the ejectors 14a, 14b are used to direct a high pressure airstream over the honeycomb cells. The high pressure airstream causes the inspection liquid to be dispelled also from the properly brazed cells. The light source 18 and camera 16 can again be used to determine whether any cells contain inspection liquid. Once the camera 16 confirms that all cells are empty and the part is dry, it can be removed from the pressure vessel 4. Should any defective cells have been detected, then the seal ring 12 is either discarded or sent for repair.

Figure 7:
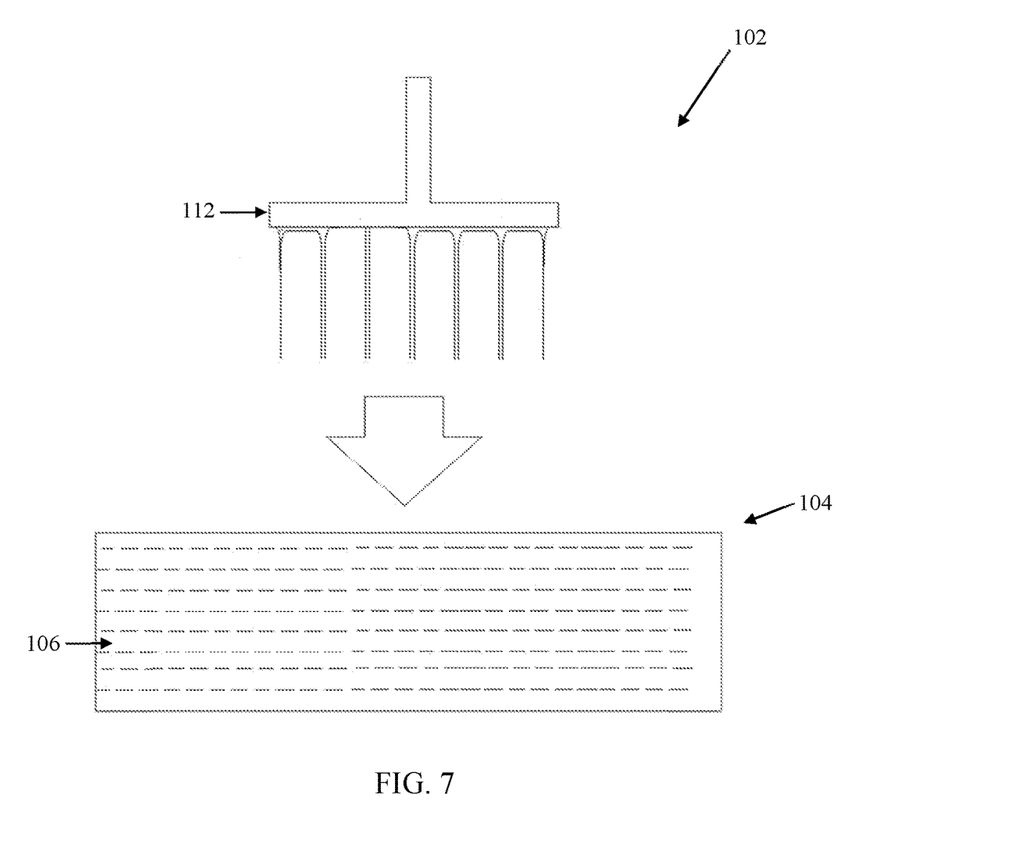
FIG. 7 is a side view of a second inspection apparatus during a first stage of inspecting a seal.

FIG. 7 shows another inspection apparatus 102. As per the inspection apparatus 2, the inspection apparatus 102 comprises a pressure vessel 104 (not fully shown) which has a lower tank section 106 which holds an inspection liquid. A honeycomb seal in the form of a segment 112 is placed in the lower tank section 106 and submerged in the inspection liquid. The seal segment 112 is arranged such that the honeycomb cells extend axially downwards towards the bottom of the lower tank section 6.

Figure 8:
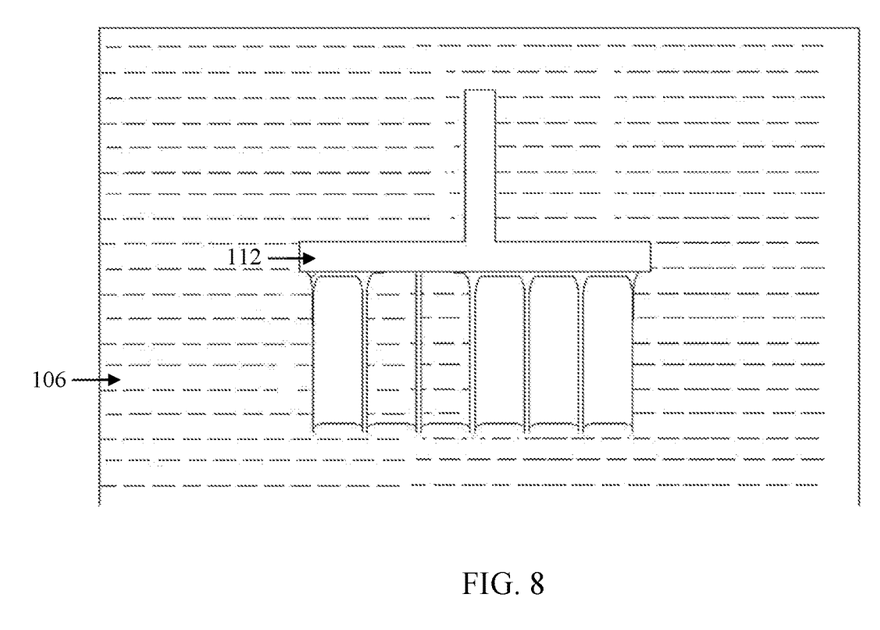
FIG. 8 is a side view of the second inspection apparatus during a second stage of inspecting the seal.

As the seal segment 112 is submerged in the inspection liquid, air is trapped within the honeycomb cells and thus prevents the inspection liquid from entering the cells. The pressure vessel 104 is sealed and the pressure in then gradually increased. The increased pressure causes the inspection liquid to compress the air trapped within the honeycomb cells. As a result, any leaks between cells as a result of poor brazes will allow air to be displaced to an adjacent cell thereby allowing the inspection liquid to fill the cells. Specifically, in FIG. 8, the second and third cells (from the left) are poorly brazed and thus allow the inspection liquid to enter, whereas the remaining (first, fourth, fifth and sixth cells) are properly brazed and thus do not allow the inspection liquid to enter.

Figure 9:
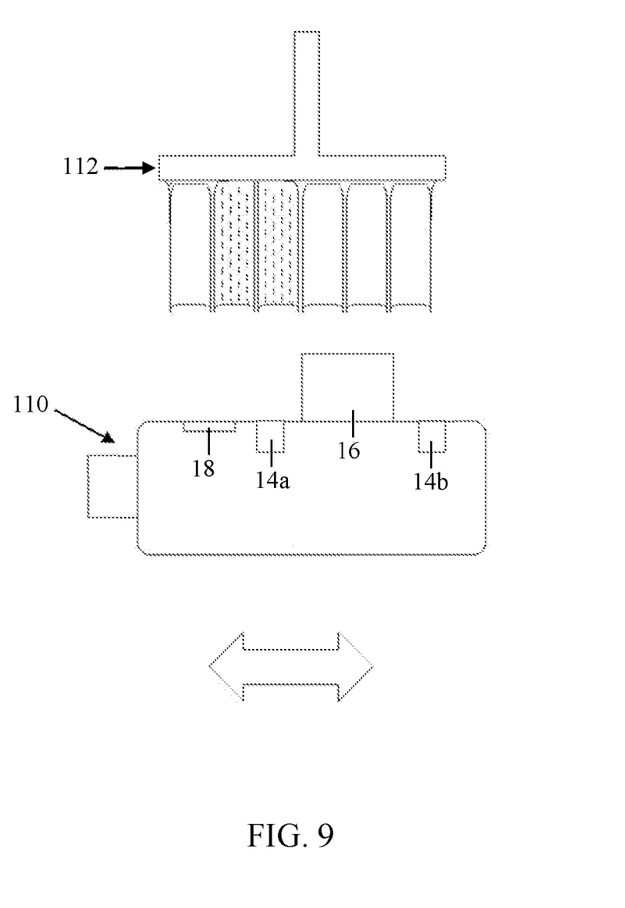
FIG. 9 is a side view of the second inspection apparatus during a third stage of inspecting the seal.

As shown in FIG. 9, as per the apparatus 2, the apparatus 102 comprises a probe 110 having a camera 116 and a light source 118. The seal segment 112 is removed from the inspection liquid and exposed to the light source 118. Cells which have leaked and thus contain the inspection liquid reflect the light back towards the probe 110 and thus appear bright to the camera 116. In contrast, properly brazed cells which have not leaked and are therefore empty do not reflect as much light back towards the probe 110 and thus appear dark to the camera 116.

As shown in FIG. 9, the probe 110 is axially translatable across the width of the pressure vessel so as to expose each and every cell to the light source 118 and camera 116. The output of the camera 116 thus allows a determination to be made as to whether each cell of the seal segment 112 is properly brazed. The position of the camera 116 allows the exact location of any defective cells to be easily identified. The low light conditions within the pressure vessel 104 aid the inspection process.

Once the inspection of the seal segment 112 is complete, the ejectors 114*a*, 114*b* are used to direct a high pressure airstream over the honeycomb cells. The high pressure airstream causes the inspection liquid to be dispelled from the improperly brazed cells. The light source 118 and camera 116 can again be used to determine whether any cells contain inspection liquid. Once the camera 116 confirms that all cells are empty and the part is dry, it can be removed from the pressure vessel 104. Should any defective cells have been detected, then the seal segment 112 is either discarded or sent for repair.

The invention is not limited to the embodiments described herein, and may be modified or adapted without departing from the scope of the present invention.

The inspection apparatus 102 may also be used to inspect a seal ring by repeating the process for several sections of the ring. Specifically, the seal ring may be oriented such that a section of the cells face downwards towards the bottom of the tank. The ring may then be stepped (by a single row of cells or several rows of cells) so that a different set of cells face downwards.

The inspection liquid may be provided in a tank which is disposed within a separate pressure vessel. The pressure vessel may have any shape and dimensions suitable to house the component being inspected. The ejectors of the probe may eject any suitable gas and are not limited to air.

Although the probe has been described as having a light source, the camera may be able to detect whether the cells are filled without using a light source. Alternatively, the light source may be separate from the probe.

Although the methods and apparatus have been described with respect to a brazed honeycomb component, it will be appreciated that they may find applications with other components. In particular, components having cellular structures bonded to an underlying substrate may be inspected using the above described methods and apparatus, regardless of whether the cellular structure is brazed to the underlying substrate or whether the cells have a honeycomb cross-section.

The invention claimed is:

1. A method of inspecting a component comprising a cellular structure bonded to a carrier substrate to form a matrix of open-ended cells, the method comprising:
    submerging the component in an inspection liquid disposed within a pressure vessel;
    changing the pressure within the pressure vessel;
    withdrawing the component from the inspection liquid; and
    determining whether the cells of the component are filled with the inspection liquid.

2. A method as claimed in claim 1, wherein the cells of the component are filled with inspection liquid when the component is submerged and the pressure in the pressure vessel is decreased so as to release trapped air from within the cells.

3. A method as claimed in claim 2, wherein a first stream of gas is directed at the cells such that the inspection liquid is displaced by the air from any cells which are not properly bonded to the carrier substrate.

4. A method as claimed in claim 3, wherein cells which are filled with the inspection liquid are properly bonded to the carrier substrate and cells which are not filled with the inspection liquid are not properly bonded to the carrier substrate.

5. A method as claimed in claim 3, wherein a second stream of gas is directed at the cells, the second stream of gas having a higher pressure than the first stream of gas such that the inspection liquid is displaced also from cells which are properly bonded to the carrier substrate.

6. A method as claimed in claim 1, wherein the component is submerged in the inspection liquid such that at least some of the cells of the component are filled with air and thus prevent the inspection liquid from entering the cells, and wherein the pressure in the pressure vessel is increased such that the trapped air is compressed and, for cells which are not properly bonded to the carrier substrate, forced into adjacent cells and replaced by inspection liquid.

7. A method as claimed in claim 6, wherein a stream of gas is directed at the cells such that the inspection liquid is displaced from cells which are not properly bonded to the carrier substrate.

8. A method as claimed in claim 1, wherein determining whether the cells of the component are filled with the inspection liquid is performed using a probe comprising a camera which is used to detect whether the cells are filled with the inspection liquid.

9. A method as claimed in claim 8, wherein the probe comprises a light source which is used to illuminate the cells being viewed by the camera.

10. A method as claimed in claim 8, wherein the probe is movable so as to direct the camera towards each of the cells of the component.

11. A method as claimed in claim 8, wherein the camera of the probe is used to detect that all of the cells are empty following inspection of the component.

12. An inspection apparatus for inspecting a component comprising a cellular structure bonded to a carrier substrate to form a matrix of open-ended cells, the apparatus comprising:
    a pressure vessel configured to contain an inspection liquid into which the component is submerged;
    a pump connected to the pressure vessel and configured to change the pressure within the vessel; and a probe comprising a camera for determining whether the cells of the component are filled with the inspection liquid.

13. An apparatus as claimed in claim 12, wherein the pump is configured to decrease the pressure in the pressure vessel so as to release trapped air from within the cells of the component which are filled with inspection liquid when the component is submerged.

14. An apparatus as claimed in claim 13, wherein cells which are filled with the inspection liquid are determined as being properly bonded to the carrier substrate and cells which are not filled with the inspection liquid are determined as being not properly bonded to the carrier substrate.

15. An apparatus as claimed in claim 13, wherein the probe further comprises a gas ejector configured to direct a first stream of gas at the cells such that the inspection liquid is displaced by the air from any cells which are not properly bonded to the carrier substrate.

16. An apparatus as claimed in claim 15, wherein the gas ejector is further configured to direct a second stream of gas at the cells, the second stream of gas having a higher pressure than the first stream of gas such that the inspection liquid is displaced also from cells which are properly bonded to the carrier substrate.

17. An apparatus as claimed in claim 12, wherein the pump is configured to increase the pressure within the pressure vessel so as to compress air trapped in the cells as the component is submerged in the inspection liquid such that the trapped air is compressed and, for cells which are not properly bonded to the carrier substrate, forced into adjacent cells and replaced by inspection liquid.

18. An apparatus as claimed in claim 17 wherein cells which are filled with the inspection liquid are determined as being not properly bonded to the carrier substrate and cells which are not filled with the inspection liquid are determined as being properly bonded to the carrier substrate.

19. An apparatus as claimed in claim 17, wherein the probe further comprises a gas ejector configured to direct a stream of gas at the cells such that the inspection liquid is displaced from cells which are not properly bonded to the carrier substrate.

20. An apparatus as claimed in claim 12, wherein the probe further comprises a light source which is used to illuminate the cells being viewed by the camera.

\* \* \* \* \*